(12) United States Patent
Pentlehner

(10) Patent No.: US 9,954,147 B2
(45) Date of Patent: Apr. 24, 2018

(54) OPTOELECTRONIC DEVICE, USE OF A DUAL EMITTER AS WAVELENGTH CONVERSION MATERIAL

(71) Applicant: OSRAM OLED GmbH, Regensburg (DE)

(72) Inventor: Dominik Pentlehner, Burghausen (DE)

(73) Assignee: OSRAM OLED GMBH, Regensburg (DE)

( * ) Notice: Subject to any disclaimer, the term of this patent is extended or adjusted under 35 U.S.C. 154(b) by 0 days.

(21) Appl. No.: 15/524,607

(22) PCT Filed: Nov. 10, 2015

(86) PCT No.: PCT/EP2015/076228
§ 371 (c)(1),
(2) Date: May 4, 2017

(87) PCT Pub. No.: WO2016/075150
PCT Pub. Date: May 19, 2016

(65) Prior Publication Data
US 2017/0324007 A1    Nov. 9, 2017

(30) Foreign Application Priority Data
Nov. 13, 2014    (DE) .................. 10 2014 116 613

(51) Int. Cl.
*H01L 33/50* (2010.01)
*C07C 211/48* (2006.01)
*C07D 209/08* (2006.01)

(52) U.S. Cl.
CPC .......... *H01L 33/502* (2013.01); *C07C 211/48* (2013.01); *C07D 209/08* (2013.01)

(58) Field of Classification Search
None
See application file for complete search history.

(56) References Cited

U.S. PATENT DOCUMENTS 7,292,614 B2    11/2007    Cok et al.
7,970,036 B2    6/2011    Linder et al.
(Continued)

FOREIGN PATENT DOCUMENTS

DE    102010006280 A1    8/2011
DE    102014103943 A1    9/2015
(Continued)

OTHER PUBLICATIONS

Grabowski, Z., et al., "Structural Changes Accompanying Intramolecular Electron Transfer: Focus on Twisted Intramolecular Charge-Transfer States and Structures," Chemical Reviews, 103 (10), Sep. 17, 2003, pp. 3899-4031.
(Continued)

*Primary Examiner* — Reema Patel
(74) *Attorney, Agent, or Firm* — Slater Matsil, LLP

(57) ABSTRACT

An optoelectronic apparatus is disclosed. In an embodiment, the apparatus includes at least one wavelength conversion region which includes at least one dual emitter as wavelength conversion material, wherein the wavelength conversion region converts primary radiation at least in part into secondary radiation, and wherein the dual emitter includes a first electronic base state and a second electronic base state, together with a first electronically excited state and a second electronically excited state which may be reached from the first electronically excited state. The dual emitter further includes emission proceeding from the second electronically excited state into the second base state.

16 Claims, 13 Drawing Sheets

(56) References Cited

U.S. PATENT DOCUMENTS

| 8,974,679 B2 | 3/2015 | Von Malm |
|---|---|---|
| 2005/0062903 A1 | 3/2005 | Cok et al. |
| 2012/0153266 A1 | 6/2012 | Thompson et al. |
| 2012/0299045 A1 | 11/2012 | Pan et al. |

FOREIGN PATENT DOCUMENTS

| EP | 1647077 B1 | 12/2007 |
|---|---|---|
| EP | 1950855 A1 | 7/2008 |
| WO | 2009036720 A1 | 3/2009 |
| WO | 2013066453 A1 | 5/2013 |
| WO | 2014136115 A1 | 9/2014 |

OTHER PUBLICATIONS

Kwon, J., et al., "Advanced Organic Optoelectronic Materials: Harnessing Excited-State Intramolecular Proton Transfer (ESIPT) Process," Advanced Materials, vol. 23, Issue 32, Jul. 22, 2011, pp. 3615-3642.

Kwon, J., et al., "Realizing Molecular Pixel System for Full-Color Fluorescence Reproduction: RGB-Emitting Molecular Mixture Free from Energy Transfer Crosstalk," J. Am. Chem. Soc., vol. 135, Nr. 30, Jul. 11, 2013, pp. 11239-11246.

Schnitzer, I, et al., "30% External Quantum Efficiency from Surface Textured, Thin-Film Light-Emitting Diodes," Applied Physics Letters, vol. 63, Issue 16, Oct. 18, 1993, pp. 2174-2176.

Zhao, Z., et al., "Dual-Fluorescent Donor-Acceptor Dyad with Tercarbazole Donor and Switchable Imide Acceptor: Promising Structure for an Integrated Logic Gate," Organic Letters, vol. 9, Nr. 4, Jan. 25, 2007, pp. 547-550.

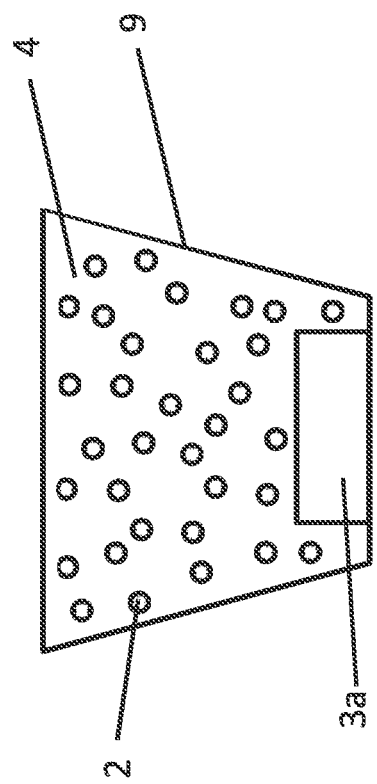

US 9,954,147 B2

OPTOELECTRONIC DEVICE, USE OF A DUAL EMITTER AS WAVELENGTH CONVERSION MATERIAL

This patent application is a national phase filing under section 371 of PCT/EP2015/076228, filed Nov. 10, 2015, which claims the priority of German patent application 10 2014 116 613.2, filed Nov. 13, 2014, each of which is incorporated herein by reference in its entirety.

TECHNICAL FIELD

The present invention relates to an optoelectronic apparatus and to the use of a dual emitter as wavelength conversion material.

BACKGROUND

Optoelectronic apparatuses such as, for example, light-emitting diodes (LEDs), for example, organic light-emitting diodes (OLEDs), organic lasers such as, for example, surface emitters ("VCSELs", vertical cavity surface emitting lasers) as well as solar cells or photodetectors may comprise wavelength conversion regions which convert primary radiation into secondary radiation.

The efficiency of optoelectronic apparatuses depends inter alia on how effectively the primary radiation is converted into secondary radiation and the extent to which loss channels, such as for instance scattering and reabsorption, which result in a reduction in luminous efficacy are present.

In particular, reabsorption of radiation, for example, of secondary radiation which has already been formed by conversion, can distinctly reduce the efficiency of wavelength conversion.

SUMMARY OF THE INVENTION

Embodiments of the invention provide an optoelectronic apparatus which permits a higher efficiency, in particular, higher efficiency of wavelength conversion.

Various embodiments provide an optoelectronic apparatus comprising at least one wavelength conversion region which comprises at least one dual emitter as wavelength conversion material, wherein the wavelength conversion region converts primary radiation at least in part into secondary radiation.

Primary radiation is, in particular, taken to be electromagnetic radiation, for example, visible light or UV light, which is emitted by a primary radiation source. The primary radiation source may, for example, be an artificial radiation source such as for instance an LED or OLED. The primary radiation source may, however, for example, also be a natural radiation source such as the sun.

When the primary radiation impinges on the at least one wavelength conversion region of the optoelectronic apparatus according to the invention, it is converted at least in part into secondary radiation, wherein the secondary radiation has a longer wavelength than the primary radiation. The primary radiation is thus of higher energy than the secondary radiation.

The dual emitter of the optoelectronic apparatus according to the invention comprises a first and a second electronic base state, together with a first electronically excited state and a second electronically excited state which may be reached from the first electronically excited state. The dual emitter furthermore comprises emission proceeding from the second electronically excited state into the second base state.

The dual emitter may, for example, comprise energy levels of the electronic states according to FIG. 1, wherein ($S_o$-1) corresponds to the first and ($S_o$-2) to the second electronic base state. ($S^*$-1) corresponds to the first and ($S^*$-2) to the second electronically excited state. The first base state ($S_o$-1) is capable of absorbing a photon of the primary radiation whereby the wavelength conversion material is converted into the first excited state ($S^*$-1). The latter can then relax into a second excited state ($S^*$-2). Secondary radiation may then arise by emission from the second excited state ($S^*$-2) into the second base state ($S_o$-2). Finally, the second base state ($S_o$-2) may pass into the first base state ($S_o$-1). The latter-stated process generally proceeds rapidly.

The secondary radiation is therefore not absorbed again (i.e., reabsorbed) by the other molecules of the wavelength conversion materials, since the second base state ($S_o$-2) thereof is not or is scarcely occupied and thus the transition ($S_o$-2)→($S^*$-2) is statistically improbable.

The inventors of the present optoelectronic apparatus have recognized that this property of dual emitters may be exploited for use as wavelength conversion materials. In this manner, it is accordingly possible to achieve a distinct reduction in reabsorption by the converter molecules of the wavelength conversion region and an increase in the proportion of secondary radiation obtained. The efficiency of wavelength conversion may accordingly be raised and the overall efficiency of the optoelectronic apparatus improved.

As a result of the higher efficiency of wavelength conversion due to the use of dual emitters instead of conventional emitters as the wavelength conversion material, it is alternatively also possible to use less of the wavelength conversion materials, so permitting material savings.

The inventors of the present invention have additionally recognized that the energy levels of the first electronic base state and of the first electronically excited state are decisive for the color appearance of the wavelength conversion region of the optoelectronic apparatus according to the invention in the off state. The energy corresponding to a transition between these states may be much higher than the energy of the secondary radiation. It is accordingly possible to provide optoelectronic apparatuses which have a neutral or transparent color appearance in the off state. This is of crucial significance, for example, in optoelectronic apparatuses which comprise LEDs or OLEDs, which may inter alia be used for displays, since a maximally neutral color appearance in the "off state" is desired in this case.

A series of further developments of the optoelectronic apparatus according to the invention are presented below.

A preferred embodiment of the optoelectronic apparatus according to the invention comprises a dual emitter, wherein the transition from the first electronically excited state into the second electronically excited state proceeds by excited state intramolecular proton transfer (ESIPT) or intramolecular charge transfer (ICT).

The inventors of the present invention have recognized that dual emitters in which intramolecular proton transfer or intramolecular charge transfer takes place are particularly highly suitable dual emitters since they have a very rapid transition from the second base state into the first electronic base state and so effectively reduce reabsorption.

A further preferred embodiment of the optoelectronic apparatus according to the invention comprises a dual emitter, wherein the transition from the first electronically excited state into the second electronically excited state proceeds faster than the radiation-emitting decay proceeding from the first electronically excited state into the first electronic base state.

If the transition proceeding from the first electronically excited state into the second electronically excited state proceeds faster than the radiation-emitting decay proceeding from the first electronically excited state into the first electronic base state, the dual emitter exhibits emission mainly from the second electronically excited state, i.e., to an extent of more than 90%, more than 95% or more than 97%.

One exemplary embodiment uses dual emitters in which the transition proceeding from the first electronically excited state into the second electronically excited state proceeds within a period of ≤10 ps, preferably ≤1 ps, which means that emission proceeds to an extent of more than 90%, particularly preferably more than 95%, most preferably more than 97% from the second excited electronic state in comparison with emission from the first excited electronic state.

The wavelength of the light emitted from these two electronically excited states may here be shifted, for example, by several tens of nm apart from one another and may have a different spectral shape. The radiation emitted from the second electronically excited state is of lower energy than the radiation emitted from the first electronically excited state (see, for example, FIG. 1).

A further embodiment relates to an optoelectronic apparatus according to the invention, wherein the transition from the second electronic base state into the first electronic base state of the dual emitter proceeds faster than excitation from the second base state into the second electronically excited state.

In dual emitters of this kind, occupation of the second electronic base state is particularly low, such that such dual emitters emit radiation from the second electronically excited state, but absorb almost no radiation which would bring about a transition proceeding from the second electronic base state into the second electronically excited state. Reabsorption is thus particularly effectively reduced.

It is here particularly preferred for said transition from the second electronic base state into the first electronic base state to proceed by means of intramolecular charge transfer or by means of intramolecular proton transfer.

In a further embodiment, the radiation-emitting region comprises ESIPT molecules as dual emitters which exhibit photo-induced keto-enol tautomerism. These ESIPT molecules may have the following general tautomeric limit formulae:

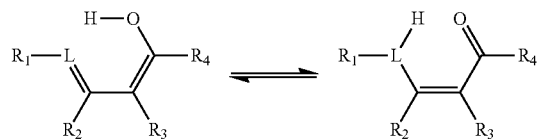

wherein L may be either nitrogen, oxygen or sulfur and $R_1$ to $R_4$ may mutually independently be hydrogen, alkyl or alkenyl groups, long-chain alkyl, alkoxy, long-chain alkoxy, cycloalkyl, haloalkyl, aryl, arylenes, haloaryl, heteroaryl, heteroarylenes, heterocycloalkylenes, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, ketoalkenyl, haloketoalkenyl, or part of a cyclic, aromatic or heteroaromatic system, for example, an anellated, cyclic aromatic or cycloaliphatic system.

The stated groups for residues $R_1$ to $R_4$ may be also themselves mutually independently substituted, wherein the substituents may in each case mutually independently be selected from the groups stated for residues $R_1$ to $R_4$. In other words, residues $R_1$ to $R_4$ may themselves have substituents which may mutually independently be hydrogen, alkyl or alkenyl groups, long-chain alkyl, alkoxy, long-chain alkoxy, cycloalkyl, haloalkyl, aryl, arylenes, haloaryl, heteroaryl, heteroarylenes, heterocycloalkylenes, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, ketoalkenyl, haloketoalkenyl, or part of a cyclic, aromatic or heteroaromatic system.

In particular, dual emitters which have such general tautomeric limit formulae may assume the enol form in the unexcited state (first base state), wherein, in the excited state of the enol form (first excited electronic state), the keto form (second excited electronic state and second base state) is then formed by intramolecular proton transfer.

General definition of groups: general groups, such as, for example, alkyl, alkoxy, aryl etc. are claimed and described in the description and claims. Unless described otherwise, the following groups within the generally described groups are preferably used for the purposes of the present invention:

Alkyl: linear and branched $C_1$-$C_8$ alkyls.
Long-chain alkyls: linear and branched $C_5$-$C_{20}$ alkyls.
Alkenyl: $C_2$-$C_6$ alkenyl.
Cycloalkyl: $C_3$-$C_8$ cycloalkyl.
Alkoxy: $C_1$-$C_6$ alkoxy.
Long-chain alkoxy: linear and branched $C_5$-$C_{20}$ alkoxy.
Alkylenes: selected from the group containing: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl.
Aryl: selected from aromatics with an aromatic nucleus, the molecular weight of which is below 300 Da.
Arylenes: selected from the group containing: 1,2-phenylene; 1,3-phenylene; 1,4-phenylene; 1,2-naphthylene; 1,3-naphthalenylene; 1,4-naphthylene; 2,3-naphthylene; 1-hydroxy-2,3-phenylene; 1-hydroxy-2,4-phenylene; 1-hydroxy-2,5-phenylene; and 1-hydroxy-2,6-phenylene.
Heteroaryl: selected from the group containing: pyridinyl; pyrimidinyl; pyrazinyl; triazolyl; pyridazinyl; 1,3,5-triazinyl; quinoninyl; isoquinoninyl; quinoxalinyl; imidazolyl; pyrazolyl; benzimidazolyl; thiazolyl; oxazolidinyl; pyrrolyl; thiophenyl; carbazolyl; indolyl; and isoindolyl, wherein the heteroaryl may be connected to the compound via each ring atom of the selected heteroaryl.
Heteroarylenes: selected from the group containing: pyridinediyl; quinolinediyl; pyrazodiyl; pyrazolediyl; triazolediyl; pyrazinediyl, thiophenediyl; and imidazolediyl, wherein the heteroarylene acts as a bridge in the compound via any desired ring atom of the heteroaryl, the following are especially preferred: pyridine-2,3-diyl; pyridine-2,4-diyl; pyridine-2,5-diyl; pyridine-2,6-diyl; pyridine-3,4-diyl; pyridine-3,5-diyl; quinoline-2,3-diyl; quinoline-2,4-diyl; quinoline-2,8-diyl; isoquinoline-1,3-diyl; isoquinoline-1,4-diyl; pyrazole-1,3-diyl; pyrazole-3,5-diyl; triazole-3,5-diyl; triazole-1,3-diyl; pyrazine-2,5-diyl; and imidazole-2,4-diyl, thiophene-2,5-diyl, thiophene-3,5-diyl; a $C_1$-$C_6$ heterocycloalkyl selected from the group containing: piperidinyl; piperidine; 1,4-piperazine, tetrahydrothiophene; tetrahydrofuran; 1,4,7-triazacyclononane; 1,4,8,11-tetraazacyclotetradecane; 1,4,7,10,13-pentaazacyclopentadecane; 1,4-diaza-7-thiacyclononane; 1,4-diaza-7-oxacyclononane; 1,4,7,10-tetraazacyclododecane; 1,4-dioxane; 1,4,7-trithiacyclononane; pyrrolidine; and tetrahydropyran, wherein the heteroaryl may be connected to the $C_1$-$C_6$ alkyl via each ring atom of the selected heteroaryl.

Heterocycloalkylenes: selected from the group containing: piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thiacyclonon-1,4-ylene; 1,4-diaza-7-thiacyclonon-1,2-ylene; 1,4-diaza-7-thiacyclonon-2,3-ylene; 1,4-diaza-7-thiacyclonon-6,8-ylene; 1,4-diaza-7-thiacyclonon-2,2-ylidene; 1,4-diaza-7-oxacyclonon-1,4-ylene; 1,4-diaza-7-oxacyclonon-1,2-ylene; 1,4-diaza-7-oxacyclonon-2,3-ylene; 1,4-diaza-7-oxacyclonon-6,8-ylene; 1,4-diaza-7-oxacyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithiacyclonon-2,3-ylene; 1,4,7-trithiacyclonon-2,9-ylene; and 1,4,7-trithiacyclonon-2,2-ylidene.

Heterocycloalkyl: selected from the group containing: pyrrolinyl; pyrrolidinyl; morpholinyl; piperidinyl; piperazinyl; hexamethyleneimine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxacyclononanyl; 1,4,7,10-tetraazacyclododecanyl; 1,4-dioxanyl; 1,4,7-trithiacyclononanyl; tetrahydropyranyl; and oxazolidinyl, wherein the heterocycloalkyl may be connected to the compound via each ring atom of the selected heterocycloalkyl.

Amines: the group —N(R)$_2$ wherein each R is independently selected from: hydrogen; $C_1$-$C_6$ alkyl; $C_1$-$C_6$-alkyl-$C_6H_5$; and phenyl, wherein if both instances of R' are $C_1$-$C_6$ alkyl, the two instances of R' may form an NC$_3$ to NC$_5$ heterocyclic ring, wherein the remaining alkyl chain forms an alkyl substituent on the heterocyclic ring.

Haloalkyl: selected from the group containing mono-, di-, tri-, poly and perhalogenated linear and branched $C_1$-$C_8$ alkyl, in particular, —CF$_3$.

Pseudohalogen: selected from the group containing —CN, —SCN, —OCN, N$_3$, —CNO and —SeCN.

Aryl: selected from the group containing: phenyl; biphenyl; naphthalenyl; anthracenyl; and phenanthrenyl.

Arylenes: selected from the group containing: 1,2-phenylene; 1,3-phenylene; 1,4-phenylene; 1,2-naphthylene; 1,4-naphthalenylene; 2,3-naphthylene and 1-hydroxy-2,6-phenylene.

Heteroaryl: selected from the group containing: pyridinyl; pyrimidinyl; quinoninyl; pyrazolyl; triazolyl; isoquinoninyl; imidazolyl; and oxazolidinyl, wherein the heteroaryl may be connected to the compound via each ring atom of the selected heteroaryl.

Heteroarylenes: selected from the group containing: pyridine-2,3-diyl; pyridine-2,4-diyl; pyridine-2,6-diyl; pyridine-3,5-diyl; quinoline-2,3-diyl; quinoline-2,4-diyl; isoquinoline-1,3-diyl; isoquinoline-1,4-diyl; pyrazole-3,5-diyl; and imidazole-2,4-diyl.

Heterocycloalkyl: selected from the group containing: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heteroaryl may be connected to the compound via each ring atom of the selected heteroaryl.

Heterocycloalkylenes: selected from the group containing: piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrrolidin-2,5-ylene; pyrrolidin-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,1043-pentaazacyclopentadec-1,4-ylene; 1,4,7,10,13-pentaazacyclopentadec-1,7-ylene; 1,4-diaza-7-thiacyclonon-1,4-ylene; 1,4-diaza-7-thiacyclonon-2,3-ylene; 1,4-diaza-7-thiacyclonon-2,2-ylidene; 1,4-diaza-7-oxacyclonon-1,4-ylene; 1,4 diaza-7-oxacyclonon-2,3-ylene; 1,4-diaza-7-oxacyclonon-2,2-ylidene; 1,4-dioxan-2,6-ylene; 1,4-dioxan-2,2-ylidene; tetrahydropyran-2,6-ylene; tetrahydropyran-2,5-ylene; and tetrahydropyran-2,2-ylidene, a —$C_1$-$C_6$-alkylheterocycloalkyl, wherein the heterocycloalkyl is selected from the group containing: piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and pyrrolidinyl, wherein the heterocycloalkyl may be connected to the compound via each ring atom of the selected heterocycloalkyl.

In particular, the following molecules may be used as ESIPT molecules: benzoxazoles and benzothiazoles, in particular, 2-(2-hydroxyphenyl)-benzothiazole, 2-(2'-hydroxyphenyl)benzoxazole and the derivatives thereof, which are linked to other aromatic rings, such as, for example, phenyl, pyridine, napththyl, quinoline, indole, pyrazine, acridine, anthracene, benzo[a]pyrene, fluoranthene, fluorene, pyrene, chrysene, phenanthrene, which have a hydroxyl or thiol group in position 2.

Molecules with the following structures or tautomeric limit formulae may, in particular, also be used as ESIPT molecules:

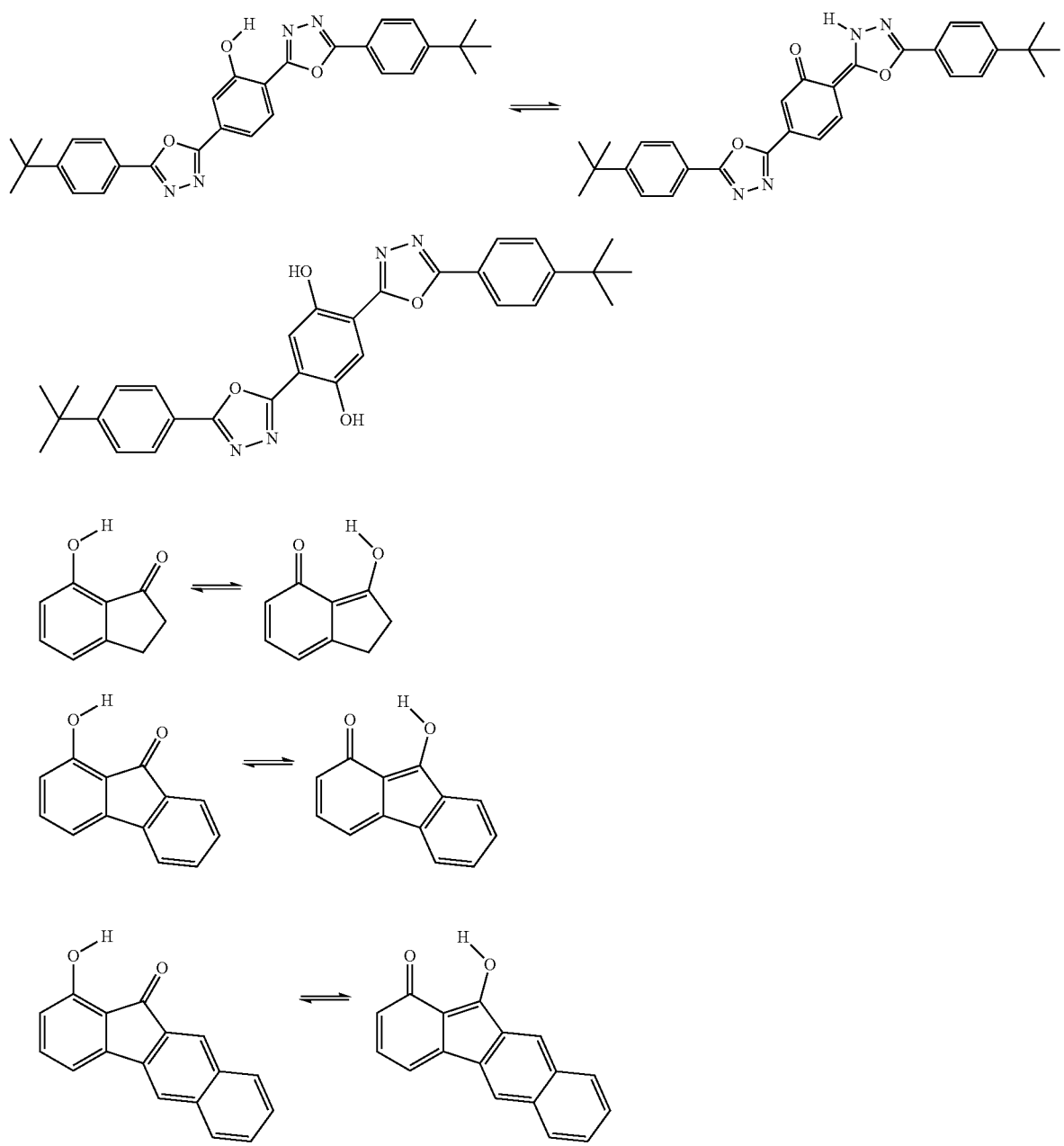

In another, preferred embodiment of the optoelectronic apparatus according to the invention, the dual emitter exhibits intramolecular charge transfer (ICT) which is inducible between at least one electron acceptor group and an electron donor group.

The inventors of the present invention have recognized that such molecules (ICT molecules) are particularly highly suitable dual emitters for use as wavelength conversion materials, since they suppress reabsorption particularly effectively.

ICT molecules which may be used in the organic optoelectronic apparatuses of the present invention, in particular, have the following general structural formulae:

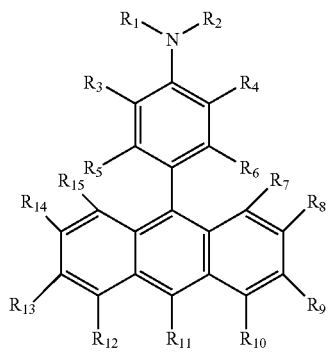

I

-continued

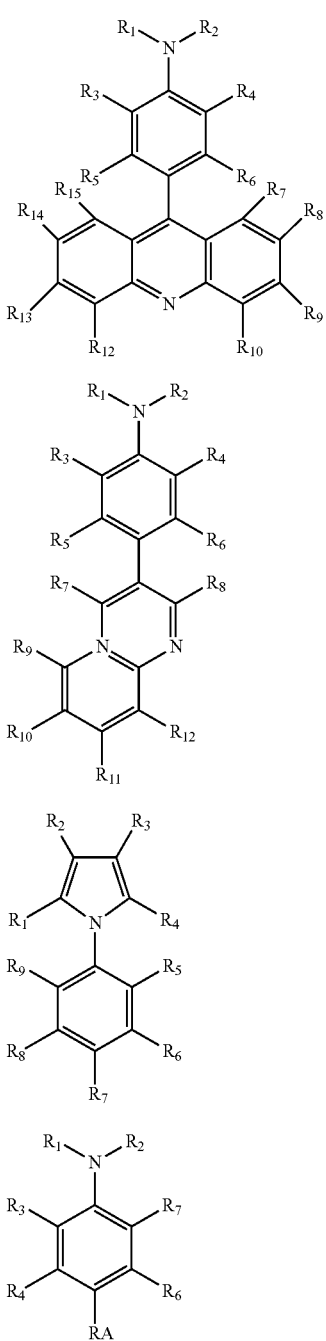

The substituents $R_1$ to $R_{15}$ may here have the above meanings of substituents $R_1$ to $R_4$, wherein, in particular, substituents $R_7$ to $R_{15}$ on the anthracene ring or the substituents on the acridine ring may in each case mutually independently also be hydrogen.

Throughout the application, hydrogen may, in addition to being normal hydrogen ($^1$H), also be deuterium ($^2$H).

Substituent $R_{11}$ in the anthracene ring of formula I or substituent $R_7$ in formula IV may also be an electron-attracting group RA, for example, —CN, —SCN, or halogen. The substituents may furthermore also be bridged to one another.

ICT molecules which may, in particular, be used for the dual emitters are also the compounds which are stated on pages 3976 to 4031 of the review article "Structural Changes Accompanying Intramolecular Electron Transfer: Focus on Twisted Intramolecular Charge-Transfer States and Structures", Grabowski et al. Chem. Rev. 2003, 3899 to 4031, to the full content of which reference is hereby made.

The ICT molecules may, in particular, comprise electron donor and electron acceptor groups in the molecule via which intramolecular charge transfer proceeds. ICT molecules which may, for example, be used are molecules with the following structures:

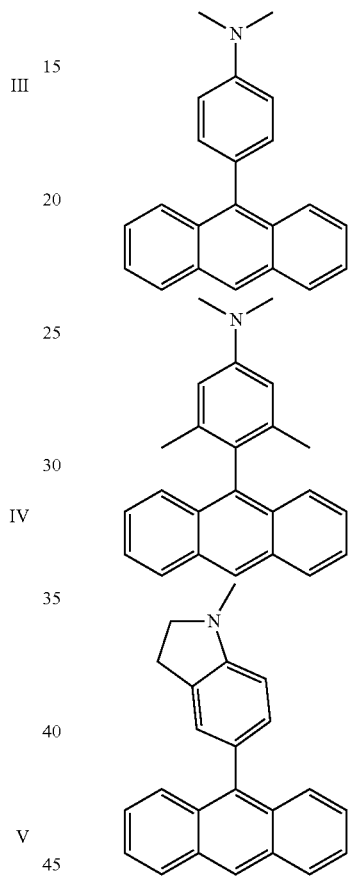

The primary and/or secondary radiation may comprise one or more wavelengths or wavelength ranges in an infrared to ultraviolet wavelength range, in particular, in a visible wavelength range. It is, for example, possible for the spectrum of the primary radiation and/or secondary radiation to be narrowband, i.e., for the primary radiation and/or secondary radiation to have a wavelength range which is or approaches monochromatic. The spectrum of the primary radiation and/or secondary radiation may alternatively also be broadband, i.e., the primary radiation and/or secondary radiation may have a polychromatic wavelength range, wherein the polychromatic wavelength range may have a continuous spectrum and/or a plurality of discrete spectral components with different wavelengths.

In a further refinement of the optoelectronic apparatus according to the invention, the wavelength conversion region comprises a matrix material in addition to the dual emitter.

In particular, the dual emitter may be homogeneously distributed in the matrix material.

In a further refinement of the optoelectronic apparatus according to the invention, the matrix material is not electrically conductive. Since the wavelength conversion material is not excited by application of an electrical field or by means of current flow, but instead by means of the photons of the primary radiation, the wavelength conversion material need not be surrounded with an electrically conductive matrix.

Instead, it is possible to use many different matrix materials, preferably with high transparency, which need not be or are not electrically conductive. This permits a wider variety of usable matrix materials.

In one particularly preferred further development, the wavelength conversion region comprises a matrix material which is selected from the group comprising curable organic materials, in particular, siloxanes, epoxides, acrylates, methyl methacrylates, imides, carbonates, olefins, styrenes, urethanes or derivatives thereof in the form of monomers, oligomers or polymers and furthermore also mixtures or copolymers thereof.

For example, the matrix material may comprise or be an epoxy resin, polymethyl methacrylate (PMMA), polystyrene, polycarbonate, polyacrylate, polyurethane or a silicone resin such as for instance polysiloxane or mixtures thereof.

Alternatively or additionally, the matrix material may also comprise inorganic materials.

In a further development of the optoelectronic apparatus according to the invention, the dual emitter additionally emits radiation from the first excited electronic state, as well as the emission already mentioned above from the second excited state. Dual emission may thus be observed. Accordingly (see energy level diagram in FIG. 1), both transitions $(S^*\text{-}1) \rightarrow (S_o\text{-}1)$
$(S^*\text{-}2) \rightarrow (S_o\text{-}2)$ may be present simultaneously.

The inventors have recognized that the relative ratio of the two contributions to one another from the matrix of the conversion region into which the dual emitter is introduced is dependent on the nature of the dual emitter and the frequency of the excitation light (primary beam).

A higher frequency of the excitation light accordingly promotes the transition from the first into the second electronically excited state. This results in a higher proportion of the emission from the second electronically excited state.

Intramolecular proton transfer in the electronically excited state (ESIPT), is promoted by protic matrix materials. Intramolecular charge transfer (ICT) is promoted by polar matrix materials. The relative ratio of the two types of radiation may thus be influenced by suitable selection of the matrix material.

The inventors of the present optoelectronic apparatus have additionally recognized that the simultaneous presence of both transitions may be exploited in order to generate desired mixtures of different types of radiation.

The inventors of the present invention have, in particular, established that the use of dual emitters as wavelength conversion materials in optoelectronic apparatuses may be purposefully exploited for generating two types of radiation of different colors.

In this manner, it is, for example, possible to generate differently colored types of radiation with just one wavelength conversion material instead of with two different conventional wavelength conversion materials. Conventional wavelength conversion materials should here and hereinafter be taken to mean inorganic or organic wavelength conversion materials, furthermore quantum dots, which emit from just one excited state.

In the case of the present invention, one dual emitter is sufficient for generating 2 colors by conversion.

The primary radiation may, for example, comprise blue light. The blue light may be absorbed by the dual emitter which is in turn capable of emitting from both excited states. For example, it is possible for the dual emitter to emit green light from the first excited state (according to FIG. 1 corresponding to the transition: $(S^*\text{-}1) \rightarrow (S_o\text{-}1)$) and red light from the second excited state (according to FIG. 1 corresponding to the transition: $(S^*\text{-}2) \rightarrow (S_o\text{-}2)$).

In a further preferred embodiment, portions of incompletely converted primary radiation may form a mixture of types of radiation together with the generated secondary radiation.

Color mixtures are, for example, accordingly possible which are obtained from a mixture of visible light of differing wavelength. This may, for example, be exploited for generating white light.

A further embodiment of the optoelectronic apparatus according to the invention comprises, in addition to a first dual emitter, a second dual emitter which differs from the first. It is, for example, also possible for even more than two different dual emitters to be used.

The wavelength conversion region may, for example, comprise the two different dual emitters.

Such optoelectronic apparatuses permit still greater latitude in the superposition and conversion of primary and/or secondary radiation. In this manner, mixtures of a plurality of different types of radiation may, for example, be made possible. Moreover, secondary radiation which has been formed from the primary radiation in the first wavelength conversion region may be further converted into tertiary radiation in the second wavelength conversion region.

In another development of the invention, a conventional wavelength conversion material is also present in addition to the dual emitter. In this manner too, it is possible for greater latitude in mixing effects to be achieved or for conversion into tertiary radiation to proceed.

If, in addition to the dual emitter, a conventional wavelength conversion material is present, it is particularly preferable for the energy of the one transition of the conventional wavelength conversion material to be located between the energies of the two transitions of the dual emitter.

In other words, the energy which corresponds to an emission from the first excited state of the dual emitter is greater than the energy of the emission of the conventional wavelength conversion material. Moreover, the energy which corresponds to an emission from the second excited state of the dual emitter is lower than the energy of the emission of the conventional wavelength conversion material. Energy transfer processes between the dual emitters and the conventional wavelength conversion material are very largely suppressed in this manner.

It is, for example, possible to achieve particularly high CRI values with such optoelectronic apparatuses. CRI here denotes color rendering index, which is an indicator of the quality of the color rendering of a light source.

One particularly preferred embodiment relates to an optoelectronic apparatus according to the invention in which the dual emitter and a conventional wavelength conversion material are jointly present in the same wavelength conversion region.

In another further development of the optoelectronic apparatus according to the invention, at least 75%, in particular, 90%, furthermore preferably at least 95% and most preferably at least 98% of the primary radiation is converted into secondary radiation. Full conversion or degrees of conversion approaching full conversion are thus achieved.

The inventors of the present invention have established that, in particular, at high degrees of conversion, for example, at full conversion, it is possible by using dual emitters to achieve a particularly clear improvement in the efficiency of wavelength conversion in comparison with conventional wavelength conversion materials.

In conventional optoelectronic apparatuses, particularly high concentrations of wavelength conversion materials are used in wavelength conversion regions in order to achieve high degrees of conversion. In the case of conventional wavelength conversion materials, however, reabsorption also increases hand in hand with increasing concentration, because more molecules of the wavelength conversion materials which can be excited by the radiation are then located in the beam path. Alternatively, the thickness of the wavelength conversion region is increased in conventional optoelectronic apparatuses. This, however, results in other undesired losses, for example, due to absorption of the radiation by the matrix in which the wavelength conversion materials are embedded.

Since using dual emitters in the optoelectronic apparatus according to the invention is capable of reducing the reabsorption loss channel, it is accordingly possible, in particular, at high degrees of conversion, for example, at full conversion, to achieve a distinct increase in efficiency in comparison with conventional optoelectronic apparatuses.

Since a distinct reduction in reabsorption can be achieved even at high wavelength conversion material concentrations when using dual emitters, the wavelength conversion material may be used in excess. This has the advantage that it is consequently possible to dispense with filters which, in conventional systems, have to be arranged downstream of the optoelectronic apparatus in order to remove residual primary radiation. It is possible to dispense with using such filters in the optoelectronic apparatus according to the invention, resulting in reduced manufacturing effort and lower materials costs. It is also possible in this manner to achieve the same secondary radiation power at a lower primary radiation power. This permits an increased service life of the optoelectronic apparatus.

In this manner, the service life of the wavelength conversion layer or of the entire wavelength conversion region may be increased by using dual emitters. Accordingly, for example, no color modification occurs due to degradation processes.

In a further refinement of the optoelectronic apparatus according to the invention, at least some of the primary and/or secondary radiation passes repeatedly through the wavelength conversion region.

In particular, in optoelectronic apparatuses in which the attempt is made to improve light outcoupling on the basis of scattering, for example, in OLEDs with internal or external outcoupling, the radiation often passes repeatedly through a wavelength conversion region.

Repeated passage of primary and/or secondary radiation through the wavelength conversion region is, for example, possible if the wavelength conversion region is arranged between at least partially reflective regions. In conventional optoelectronic apparatuses, in which the radiation passes repeatedly through the wavelength conversion region, reabsorption plays a particularly large role and results in distinct losses in intensity of the resultant radiation. This is attributable to the beam impinging multiple times on the wavelength conversion molecules present in the wavelength conversion region on repeated passage, wherein, in addition to the desired wavelength conversion, reabsorption may also occur to a greater extent.

Therefore, as a result of a reduction in reabsorption by use of a dual emitter as wavelength conversion material, in particular, in optoelectronic apparatuses in which the primary and/or secondary radiation passes repeatedly through the wavelength conversion region, it is possible to achieve a particularly distinct improvement in the efficiency and intensity of the resultant radiation.

This is of great significance, for example, in the field of laser technology, for instance in organic lasers. VCSEL lasers as surface emitters may be mentioned as an important example which distinctly benefit from the use of dual emitters.

One embodiment of the optoelectronic apparatus according to the invention comprises a functional region (3) (see, for example, FIG. 2), wherein the functional region may be a primary radiation source (3a) (see, for example, FIG. 8) or a photoactive region (3b) (see, for example, FIG. 9).

It is generally the case for all embodiments of the description that the wavelength conversion region(s) may be arranged both directly on the functional region (3) or may be separated from the functional region (3) by intermediate regions or intermediate layers. Materials with high transparency may, in particular, considered as materials for intermediate regions or intermediate layers. In the case of a plurality of wavelength conversion regions, said regions may also be separated from one another by intermediate regions or may be arranged directly on top of one another.

Another further development of the optoelectronic apparatus according to the invention comprises at least two wavelength conversion regions.

One particularly preferred further development relates to an optoelectronic apparatus with two different wavelength conversion regions, wherein the first region comprises a dual emitter, while the second region comprises either a conventional wavelength conversion material or likewise a dual emitter. This permits greater latitude in possible radiation combinations and conversions.

In one development, the at least two wavelength conversion regions may be arranged one above the other. The variety of possible conversions and mixtures may be increased in this manner.

In one development which differs therefrom, the at least two wavelength conversion regions may be arranged adjacent one another on the functional region.

A further embodiment relates to an optoelectronic apparatus according to the invention wherein the optoelectronic apparatus comprises a primary radiation source which is selected from the group comprising:

organic light-emitting diodes (OLEDs)

inorganic light-emitting diodes (LEDs)

lasers, in particular, surface emitters (vertical cavity surface emitting lasers (VCSELs)), for example, organic lasers, wherein the primary radiation source emits the primary radiation which is converted at least in part into secondary radiation by the wavelength conversion region.

In this case, the primary radiation source is a component of the optoelectronic apparatus (FIG. 8), wherein the wavelength conversion region is, however, not part of the primary radiation source itself.

One particularly preferred further development relates to an optoelectronic apparatus according to the invention which comprises a primary radiation source which is an organic light-emitting diode (OLED) (see FIG. 10a), wherein the OLED emits the primary radiation which is converted at least in part into secondary radiation in the wavelength conversion region. In this embodiment, the wavelength conversion region is not part of the OLED itself. In particular, the wavelength conversion region is not arranged between the electrodes of the OLED and is thus not exposed to electric fields and currents.

In an embodiment which differs therefrom of the optoelectronic apparatus according to the invention, the apparatus itself takes the form of an organic light-emitting diode (OLED) (see FIG. 10b). In addition to the wavelength conversion region, the optoelectronic apparatus here additionally comprises a first electrode, a second electrode and a radiation-emitting region which differs from the wavelength conversion region, wherein both the radiation-emitting region and the wavelength conversion region are arranged between the first and second electrodes. If the wavelength conversion region is arranged between the two electrodes, the matrix material may be selected such that it is electrically conductive, i.e., is capable of conducting electrons and/or "holes".

The inventors of the present invention have recognized that, under certain circumstances, even when the wavelength conversion region is arranged between the electrodes the dual emitter does not degrade, even in the case of a dual emitter which would degrade in an arrangement directly in the radiation-emitting region. What is crucial here is that the wavelength conversion region is not part of the radiation-emitting region, i.e., of the region in which electrons and "holes" predominantly recombine (for example, to an extent of more than 90%). For example, the dual emitter may be part of hole-transporting, hole-injecting or hole-blocking layers. The dual emitter may also be part of electron-transporting, electron-injecting or electron-blocking layers. In other words, in this case, due to the presence of the wavelength conversion material, said layers simultaneously perform the function of a wavelength conversion region in addition to their conventional function. Even if the wavelength conversion region is arranged between the electrodes, the wavelength conversion material is here primarily excited by the primary radiation.

In the refinement of the optoelectronic apparatus just described as an OLED with the wavelength conversion region and the radiation-emitting region which differs therefrom which are both arranged between the electrodes, it is furthermore particularly preferred for there additionally to be a layer between the radiation-emitting region and the wavelength conversion region which separates the radiation-emitting region and the wavelength conversion region from one another, such that the two regions are not arranged directly on top of one another. For example, at least one charge carrier-blocking layer may be arranged between the radiation-emitting region and the wavelength conversion region. Thanks to the presence of at least one interlayer, it is possible to ensure that charge carriers, electrons and "holes" are not simultaneously present at high concentration in the wavelength conversion region. Thanks to the presence of the interlayer, it may thus be ensured that the charge carriers recombine only to a very small extent (i.e., for example, to an extent of less than 10%, in particular, less than 5%, more preferably less than 2% or ideally not at all) in the wavelength conversion region.

It is thus possible for the optoelectronic apparatuses according to the invention to take the form of an OLED and to comprise at least one wavelength conversion region between the electrodes of the OLED (FIG. 10b), or for the wavelength conversion region to be arranged outside the OLED which forms the primary radiation source (FIG. 10a).

It is in each case, for example, possible for an optoelectronic apparatus according to the invention to comprise an OLED which emits blue light as primary radiation. The blue light may be converted by the dual emitter in the wavelength conversion region at least in part or, for the purposes of full conversion, completely (i.e., at least to a degree of conversion of greater than 90%) into red light. The red light is here, for example, obtained by the transition from the second electronically excited state into the second electronic base state of the dual emitter, i.e., according to FIG. 1 by the transition $(S^*\text{-}2) \rightarrow (S_o\text{-}2)$. The wavelength conversion region thus absorbs blue light and emits red light. In this manner, it is possible to provide an outwardly red-emitting optoelectronic apparatus which, in the off state has a color appearance comparable to that of a blue OLED, i.e., a neutral or transparent color appearance. This is, in particular, highly advantageous for applications for instance for screens and displays where a maximally neutral color appearance is desired the off state. Transparent OLEDs with a neutral off state may furthermore be obtained using dual emitters as wavelength conversion materials.

This effect, which has already been mentioned previously, is not limited to the colors described here. The stated example is merely illustrative.

In addition, said effect occurs not only on emission from the second excited state, but also when dual emission, i.e., emission from the first and second electronically excited states, is used, the color appearance substantially being determined by the transition from the first electronically excited state of the dual emitter (transition: $(S^*\text{-}1) \rightarrow (S_o\text{-}1)$ in FIG. 1).

It is alternatively also possible for the optoelectronic apparatus according to the invention to comprise an inorganic light-emitting diode (LED) as primary radiation source.

The LED may, for example, be a thin-film light-emitting diode chip. A thin-film light-emitting diode chip is distinguished, in particular, by the following characteristic features:

a reflective layer is applied to or formed on a first major surface, facing a carrier element, of a radiation-generating, epitaxial layer sequence, said reflective layer reflecting at least some of the electromagnetic radiation generated in the epitaxial semiconductor layer sequence back into it;

the epitaxial layer sequence has a thickness in the region of 20 µm or less, in particular, in the region of 10 µm; and the epitaxial layer sequence contains at least one semiconductor layer with at least one area which comprises an intermixing structure, which ideally leads to an approximately ergodic distribution of the light in the epitaxial layer sequence, i.e., it exhibits scattering behavior which is as ergodically stochastic as possible.

The basic principle of a thin-film light-emitting diode chip is described, for example, in I. Schnitzer et al., Appl. Phys. Lett. 63 (16), 18 Oct. 1993, 2174-2176, the disclosure content of which is hereby included in this respect by reference.

The same color appearance benefits with regard to the off state as have just been described for the optoelectronic apparatus with an OLED as primary radiation source are obtained here too.

In addition to OLEDs and LEDs, in a further embodiment lasers may also serve as primary radiation sources which emit the primary radiation which impinges on the wavelength conversion region.

An embodiment of the optoelectronic apparatus according to the invention which differs therefrom is distinguished in that it itself takes the form of a laser and comprises a primary radiation source as pump radiation source (FIG. 12). The primary radiation source of the laser which acts as pump radiation source may, for example, be an LED or OLED. In this embodiment of the invention, the wavelength conversion region (1) is arranged as a laser-active region between two at least partially reflective regions (10a) and (10b). The laser-active region is additionally arranged in the beam path of the primary radiation source. In such a laser, reabsorption in the laser-active region may be distinctly reduced in comparison with conventional lasers by using dual emitters.

In one particularly preferred embodiment, the laser is here a VCSEL.

Another further development of the optoelectronic apparatus according to the invention comprises a photoactive region onto which the secondary radiation impinges.

The optoelectronic apparatus may, for example, be a solar cell or a photodetector.

Solar cells which comprise a wavelength conversion region can convert a larger proportion of the sunlight (primary radiation) into a frequency or wavelength range which can be converted into electrical energy by the photoactive region of the solar cell. It is thus possible to increase the efficiency of solar cells in this manner.

Sensitivity in photodetectors may be boosted in a similar manner.

In both cases, using dual emitters as the wavelength conversion material instead of conventional wavelength conversion materials permits a reduction in reabsorption, which ultimately results in the increased efficiency or sensitivity of optoelectronic apparatuses with a photoactive region.

The invention furthermore relates to the use of a dual emitter as wavelength conversion material in an optoelectronic apparatus.

Using dual emitters makes it possible to avoid reabsorption and so eliminates a central loss channel and therefore higher luminous efficacy can be achieved.

The above-stated optoelectronic apparatuses together with the claimed optoelectronic apparatuses described in the exemplary embodiments for use according to the invention are not subject to any particular exceptional conditions with regard to size, shape, material selection and technical design and therefore the selection criteria known in the field of use may be applied without restriction.

BRIEF DESCRIPTION OF THE DRAWINGS

Further details, features and advantages of the subject matter of the invention may be inferred from the following description of the figures and embodiments.

In the figures:

FIG. 11 shows a schematic side view of an embodiment of the optoelectronic apparatus according to the invention which, in addition to the wavelength conversion region (1), comprises a light-emitting diode (LED) as primary radiation source (3a).

The respective figures and embodiments are described below in greater detail for illustration.

DETAILED DESCRIPTION OF ILLUSTRATIVE EMBODIMENTS

Figure 1:
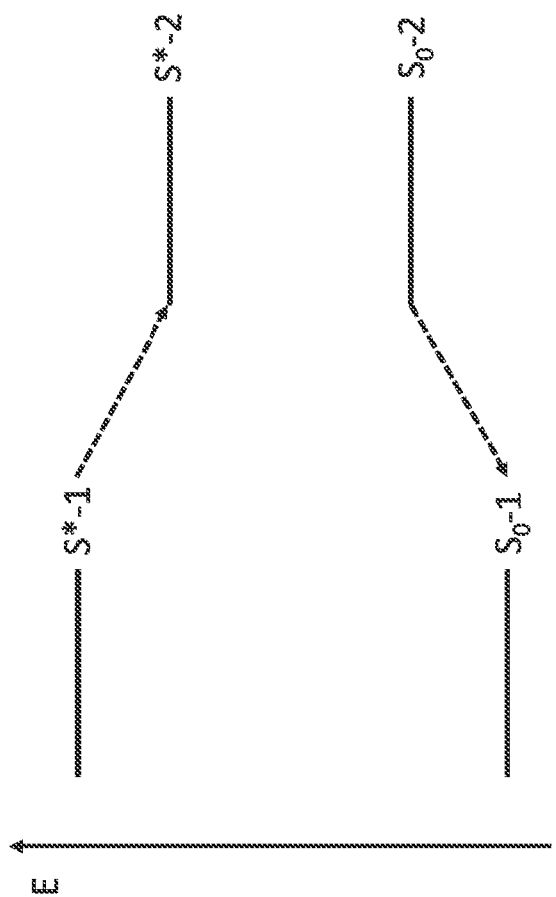
FIG. 1 shows the energy level diagram of a dual emitter according to the invention.

FIG. 1 shows the energy level diagram for a dual emitter, wherein E denotes the energy of the electronic states. Absorption of a photon induces an electronic transition from the first electronic base state ($S_o$-1) into the first electronically excited state ($S^*$-1). A transition from the first electronically excited state ($S^*$-1) into the second electronically excited state ($S^*$-2) then occurs. This transition may proceed, for example, by means of intramolecular charge transfer or intramolecular proton transfer. The dual emitter is in principle capable of emitting radiation from both electronically excited states. If the transition proceeding from the first electronically excited state ($S^*$-1) into the second electronically excited state ($S^*$-2) proceeds faster than the radiant transition from the first electronically excited state ($S^*$-1) into the first electronic base state ($S_o$-1), emission may mainly proceed from the second electronically excited state ($S^*$-2). Since the reverse reaction from the second electronic base state ($S_o$-2) into the first electronic base state ($S_o$-1) generally proceeds faster than the radiation-emitting decay proceeding from the second electronically excited state ($S^*$-2) into the second electronic base state ($S_o$-2), the second electronic base state ($S_o$-2) is scarcely populated.

The probability of an electronic transition proceeding from the second electronic base state into the second electronically excited state of the dual emitter being induced by reabsorption of radiation from other emitters, such as, for example, a further emitter, is therefore extremely low.

Figure 2:
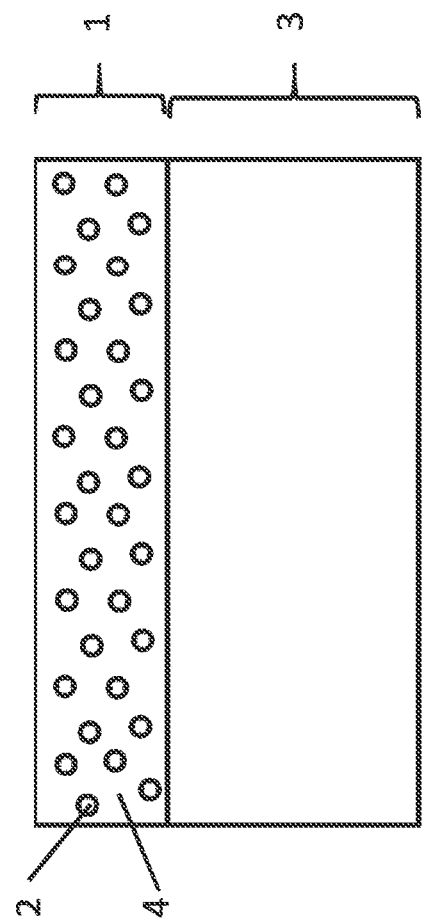
FIG. 2 shows a schematic side view of an embodiment of the optoelectronic apparatus according to the invention with wavelength conversion region (1).

FIG. 2 shows the fundamental structure of an embodiment of the optoelectronic apparatus according to the invention, comprising at least one wavelength conversion region (1). The wavelength conversion region here comprises at least one dual emitter as wavelength conversion material (2). The wavelength conversion material may here be embedded in a matrix (4). The wavelength conversion material (2) may, for example, be homogeneously distributed in the matrix material (4). The optoelectronic apparatus may furthermore comprise a functional region (3). This may be a primary radiation source (3a) or a photoactive region (3b). The wavelength conversion region (1) at least in part converts primary radiation into secondary radiation.

Figure 3:
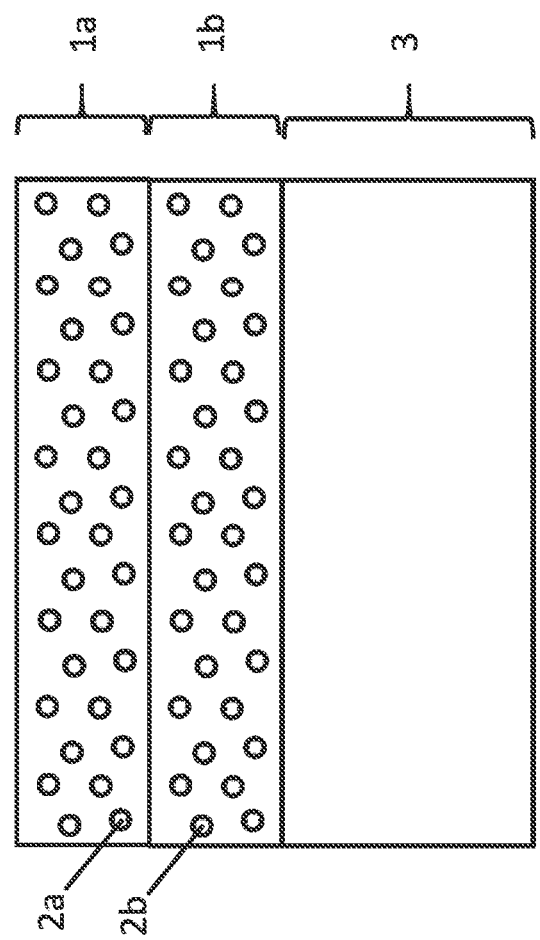
FIG. 3 shows a schematic side view of an embodiment of the optoelectronic apparatus according to the invention with two wavelength conversion regions (1a) and (1b) arranged one above the other.

FIG. 3 shows a side view of an embodiment of the optoelectronic apparatus according to the invention, comprising two wavelength conversion regions (1a) and (1b) which are arranged one above the other. These are two different wavelength conversion regions, wherein the first of the two wavelength conversion regions (1a) comprises a first dual emitter as wavelength conversion material (2a) and the second wavelength conversion region comprises a second wavelength conversion material (2b) which differs therefrom. The second wavelength conversion material (2b) may be either a conventional wavelength conversion material, i.e., a conventional emitter, which is capable of converting primary radiation into secondary radiation, or likewise a dual emitter which, however, differs from the first dual emitter (2a). Due to the superposed arrangement of the two different wavelength conversion regions, greater diversity in the mixing and conversion of primary and secondary radiation may be achieved, since the primary beam must pass through regions with different various wavelength conversion materials. It is moreover also possible for the secondary radiation formed from the primary radiation in the first wavelength conversion region to be further converted into tertiary radiation in the second wavelength conversion region.

Figure 4:
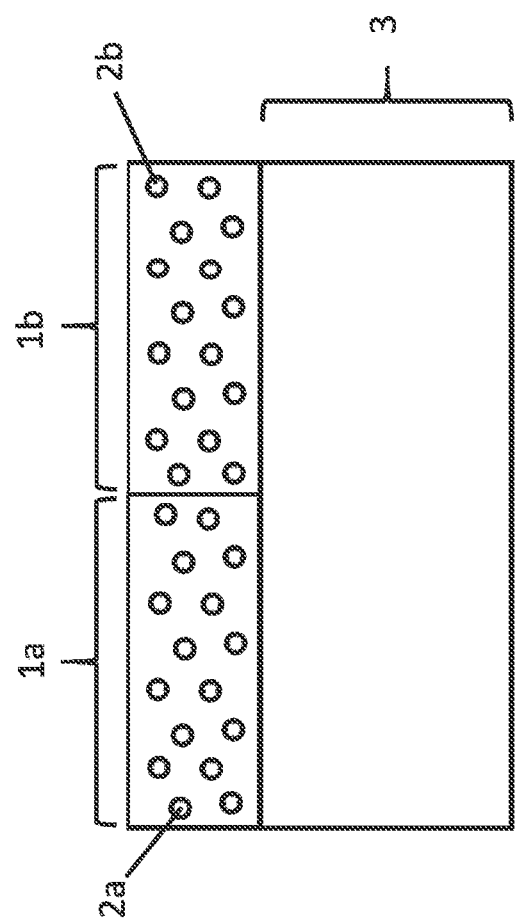
FIG. 4 shows a schematic side view of an embodiment of the optoelectronic apparatus according to the invention with two wavelength conversion regions (1a) and (1b) arranged adjacent one another.

FIG. 4 shows a side view of an embodiment of the optoelectronic apparatus according to the invention comprising two wavelength conversion regions (1a) and (1b) which are arranged adjacent one another. These are two different wavelength conversion regions, wherein the first of the two wavelength conversion regions (1a) comprises a first dual emitter as wavelength conversion material (2a) and the second wavelength conversion region comprises a second wavelength conversion material (2b) which differs therefrom. The second wavelength conversion material (2b) may again be either a conventional wavelength conversion material, i.e., a conventional emitter, which is capable of converting primary radiation into secondary radiation, or likewise a dual emitter which, however, differs from the first dual emitter (2a). Due to the side-by-side arrangement of the two different wavelength conversion regions, it is, for example, possible to ensure that primary radiation which is emitted by the functional region (3) is converted by the two different wavelength conversion regions (1a) and (1b) into two different kinds of secondary radiation. If the functional region is a photoactive region, it is possible to ensure by the adjacent arrangement that incident primary radiation undergoes a different wavelength conversion by the regions (1a) and (1b) before it impinges on the functional region (3).

Figure 5:
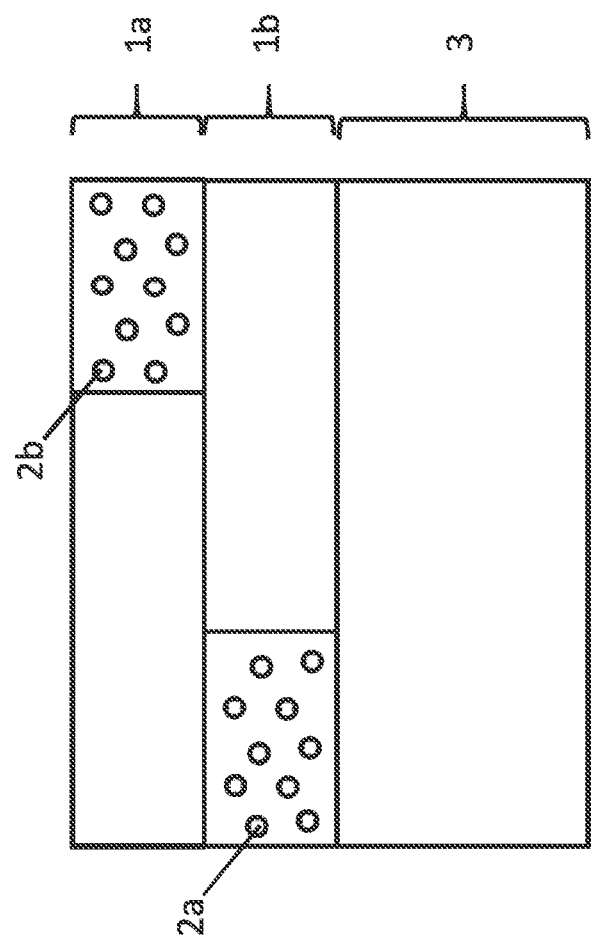
FIG. 5 shows a schematic side view of an embodiment of the optoelectronic apparatus according to the invention with two wavelength conversion regions (1a) and (1b) which have an arrangement staggered relative to one another.

FIG. 5 shows a side view of an embodiment of the optoelectronic apparatus according to the invention comprising two wavelength conversion regions (1a) and (1b) which are arranged such that they cover only parts of the functional region (3). Such an arrangement, for example, allows primary radiation which is emitted or received by the functional region (3) to be "treated" in three different ways: no treatment, wavelength conversion by the first wavelength conversion region (1a) with a first dual emitter as wavelength conversion material (2a) and wavelength conversion by a second wavelength conversion region (1b) with a second wavelength conversion material (2b) which differs therefrom.

Figure 6:
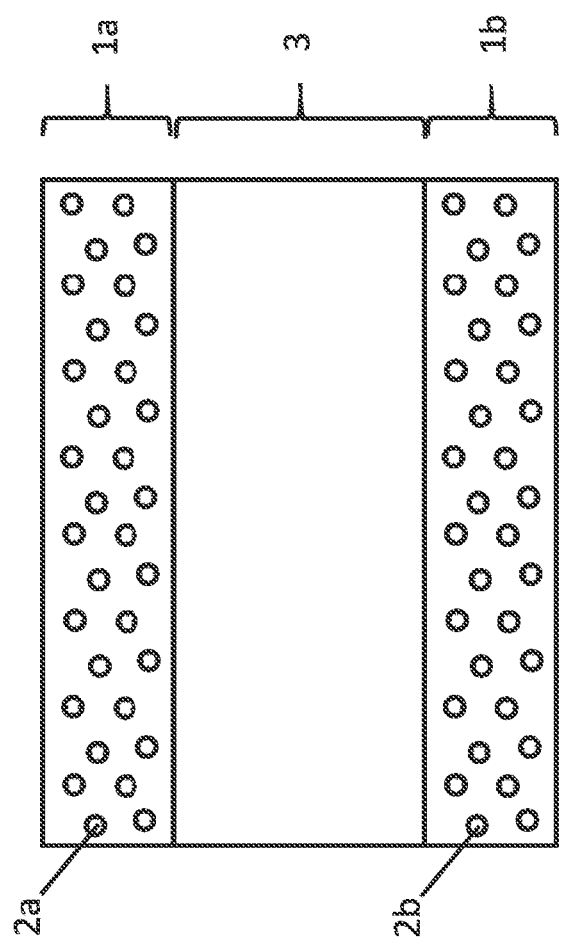
FIG. 6 shows a schematic side view of an embodiment of the optoelectronic apparatus according to the invention with two wavelength conversion regions (1a) and (1b) which are arranged above and below the functional region (3).

FIG. 6 shows a side view of an embodiment of the optoelectronic apparatus according to the invention comprising two wavelength conversion regions (1a) and (1b) which are arranged on different sides of the functional region (3). Radiation impinging on the functional region (3) from different sides or emitted by the functional region towards different sides will accordingly undergo wavelength conversion on both sides.

Figure 7:
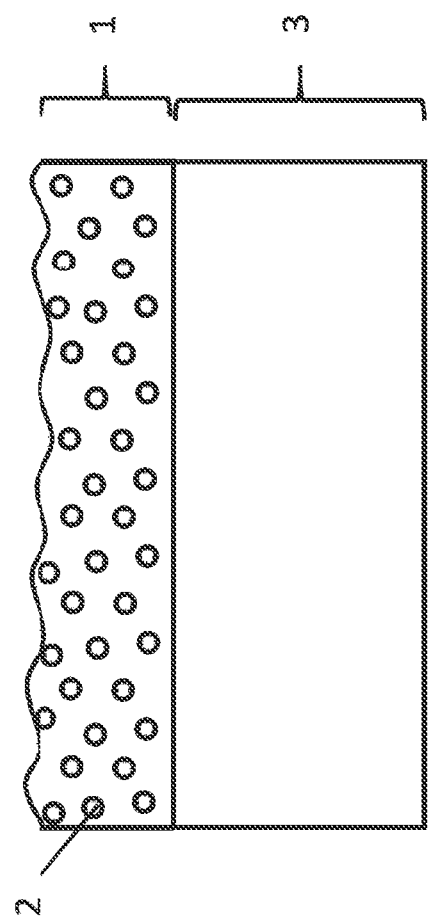
FIG. 7 shows a schematic side view of an embodiment of the optoelectronic apparatus according to the invention with a wavelength conversion region (1) comprising a surface structure with microprisms.

FIG. 7 shows a side view of an embodiment of the optoelectronic apparatus according to the invention comprising a wavelength conversion region (1), the surface of which is not smooth but instead structured. The surface structure may comprises roughened portions, trenches, prisms, for example, microprisms, lenses or truncated cones or combinations thereof which are, for example, capable of improving outcoupling of the primary and/or secondary radiation.

Figure 8:
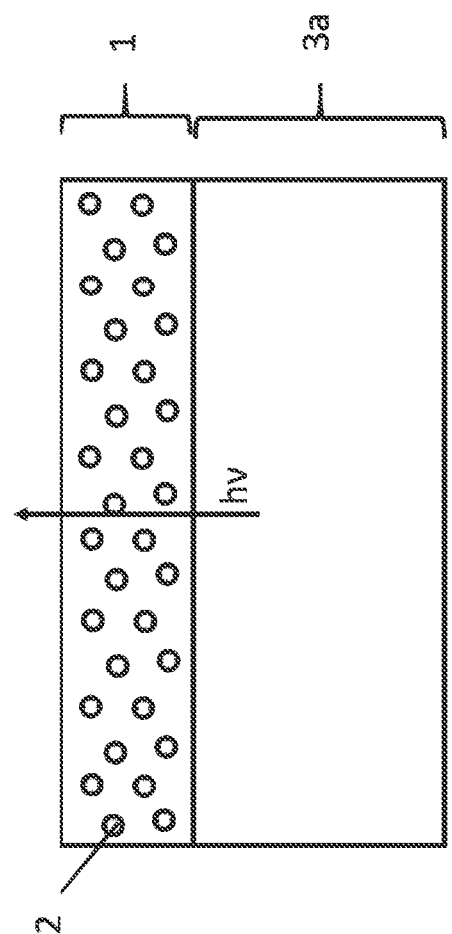
FIG. 8 shows a schematic side view of an embodiment of the optoelectronic apparatus according to the invention which, in addition to the wavelength conversion region (1), comprises a primary radiation source (3a) as functional region (3).

FIG. 8 shows a side view of an embodiment of the optoelectronic apparatus according to the invention comprising a wavelength conversion region (1) comprising a dual emitter as wavelength conversion material (2). The functional region (3) here takes the form of a primary radiation source (3a). The primary radiation source may, for example, be an inorganic LED or an OLED. Such optoelectronic apparatuses emit electromagnetic radiation (see arrow), wherein the primary radiation generated by the primary radiation source (3a) is partially or completely converted in the wavelength conversion region (1) into secondary radiation before it leaves the optoelectronic apparatus. This is thus a radiation-emitting apparatus, for example, a "conversion LED" or "conversion OLED". UV light or visible light may, for example, be converted into colored or differently colored light by the wavelength conversion region. Light from polychromatic radiation, for example, white light, may also be produced by mixing incompletely converted primary radiation with secondary radiation (or radiation from one or both transitions of the dual emitter). High CRI values are thus also achievable.

Figure 9:
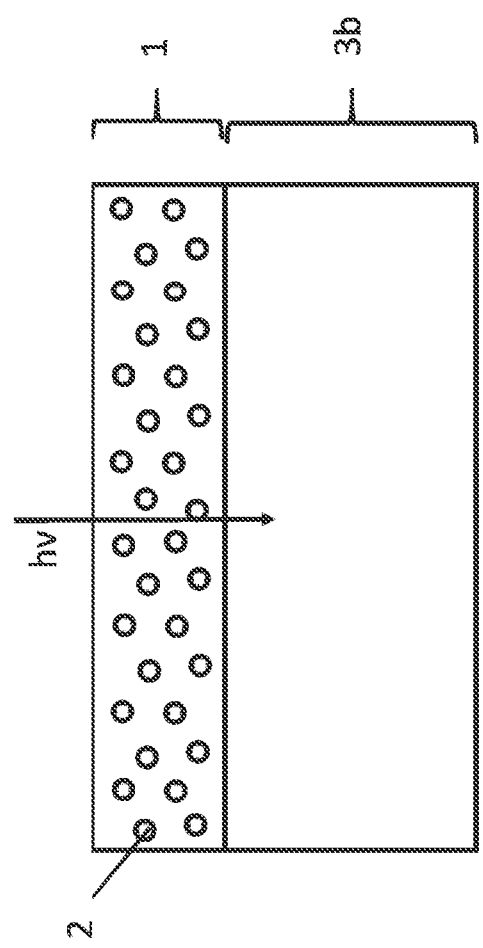
FIG. 9 shows a schematic side view of an embodiment of the optoelectronic apparatus according to the invention which, in addition to the wavelength conversion region (1), comprises a photoactive region (3b) as functional region (3).

FIG. 9 shows a side view of an embodiment of the optoelectronic apparatus according to the invention comprising a wavelength conversion region (1) comprising a dual emitter as wavelength conversion material (2). The functional region (3) here takes the form of a photoactive region (3b). Such an optoelectronic apparatus may, for example, be a solar cell or a photodetector which, with the assistance of the wavelength conversion layer, converts the incoming primary radiation (see arrow) before it impinges on the photoactive region (3b). The primary radiation may, for example, be sunlight. Thanks to the wavelength conversion of the primary radiation, the efficiency of the solar cell or the sensitivity of the photodetector may be increased, since radiation of poorly utilizable wavelength ranges may in this manner be converted into radiation which is better absorbed by the photoactive region.

Figure 10A:
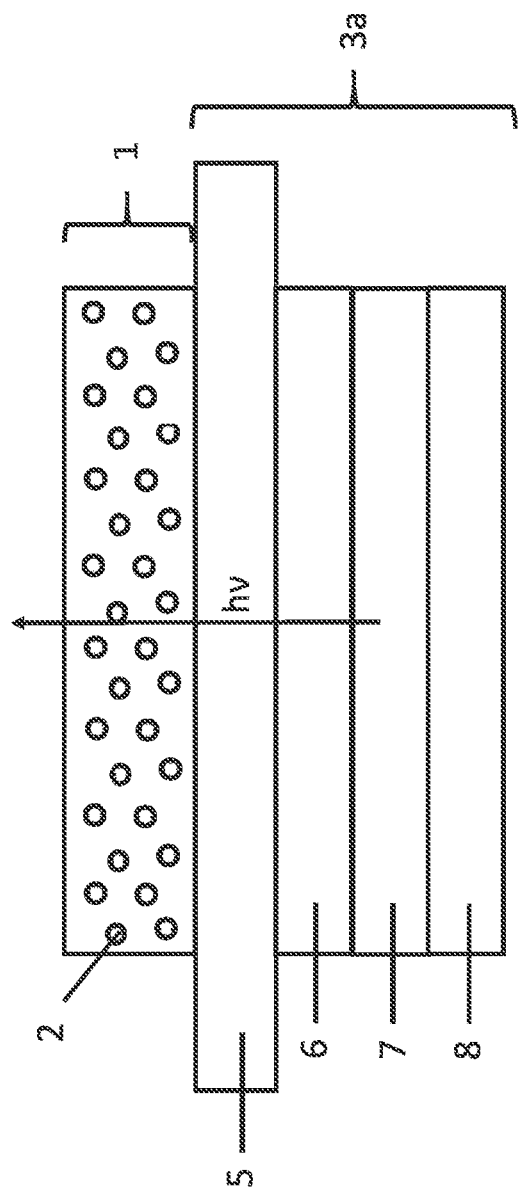
FIG. 10a shows a schematic side view of an embodiment of the optoelectronic apparatus according to the invention which, in addition to the wavelength conversion region (1), comprises an organic light-emitting diode (OLED) as primary radiation source (3a).

FIG. 10a shows a side view of a particularly preferred embodiment of the optoelectronic apparatus according to the invention comprising a wavelength conversion region (1) comprising a dual emitter as wavelength conversion material (2), wherein the primary radiation source (3a) is an OLED. The OLED comprises a substrate (5), a first electrode (6), a radiation-emitting region (7) and a second electrode (8). The organic light-emitting diode may furthermore comprise other layers, in particular, hole-transport and hole-injection layers or electron-transport and electron-injection layers and further layers conventionally used for OLEDs. Because the wavelength conversion region is arranged not between the electrodes of the OLED but instead outside the OLED, for example, is applied to the substrate, the dual emitter is not exposed to any electric currents or electric fields.

Figure 10B:
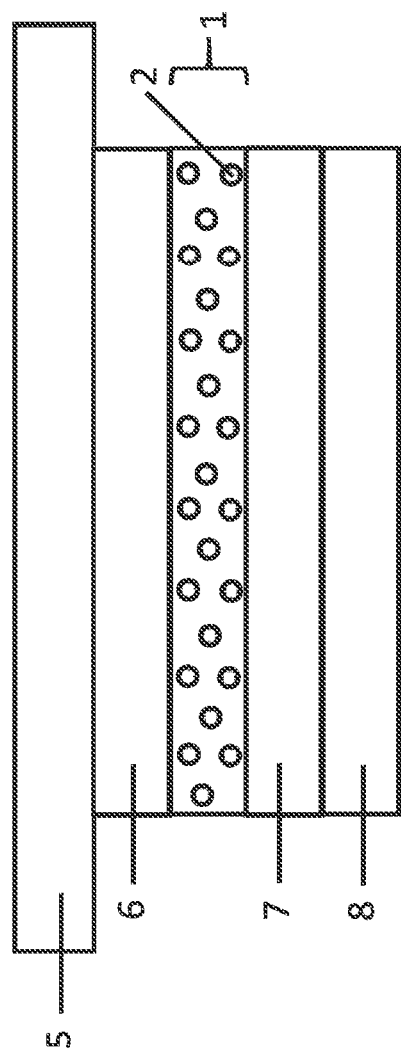
FIG. 10b shows a schematic side view of an embodiment of the optoelectronic apparatus according to the invention, in the form of an OLED, comprising, in addition to the wavelength conversion region (1), a radiation-emitting region (7) which differs from the wavelength conversion region and, like the wavelength conversion region (1), is arranged between a first (6) and a second electrode (8).

FIG. 10b shows a side view of a particularly preferred embodiment of the optoelectronic apparatus according to the invention, which differs therefrom, comprising a wavelength conversion region (1) comprising a dual emitter as wavelength conversion material (2). The optoelectronic apparatus takes the form of an OLED. The OLED comprises a substrate (5), a first electrode (6), a radiation-emitting region (7) and a second electrode (8). Both the radiation-emitting region (7) and the wavelength conversion region (1) are here arranged between the electrodes. The wavelength conversion region may here be hole-transporting, hole-injecting or hole-blocking layers which comprise the dual emitter as wavelength conversion material. The wavelength conversion region may moreover also comprise electron-transporting, electron-injecting or electron-blocking layers. Hardly any recombination of electrons and "holes" (less than 10%) occurs in the wavelength conversion region. It is, for example, possible for at least one or more intermediate layers to be present between the radiation-emitting region (7) and the wavelength conversion region (1), such that the two regions (1) and (7) are not arranged directly on top of one another. In this manner, the dual emitter is still better protected from the electrical conditions prevailing in the radiation-emitting layer (1). The organic light-emitting diode may additionally comprise further layers conventional for OLEDs.

FIG. 11 shows a schematic side view of an embodiment of an optoelectronic apparatus according to the invention, wherein the primary radiation source (3a) is an LED, for example, an LED in the form of an InGaN LED. The optoelectronic apparatus may comprise a reflector cup (9) which is capable of reflecting the radiation from the LED (3a). A matrix material (4), in which is embedded a dual emitter as wavelength conversion material (2), is arranged over the LED (3a). Matrix material (4) and wavelength conversion material (2) together form the wavelength conversion region. The dual emitter is capable of absorbing the primary radiation emitted by the LED radiation source (3a), for example, blue light, and emitting secondary radiation, for example, in the orange-red wavelength range.

Figure 12:
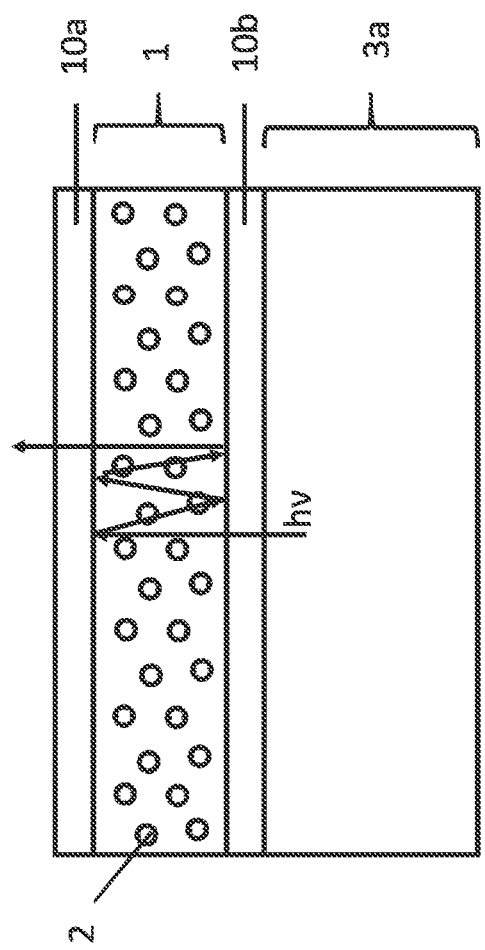
FIG. 12 shows a schematic side view of an embodiment of the optoelectronic apparatus according to the invention, in the form of a laser, for example, an organic laser.

FIG. 12 shows a schematic side view of an embodiment of an optoelectronic apparatus according to the invention which takes the form of a laser, for example, an organic laser. The wavelength conversion region (1) comprising the dual emitter (2) is here arranged as a laser-active region between partially transmissive mirrors (10a) and (10b). The radiation may pass repeatedly through the wavelength conversion region. This is shown symbolically by arrows in the representation. The laser may, for example, take the form of a VCSEL. The laser additionally comprises a primary radiation source (3a) which acts as the pump radiation source for the laser. This may be, for example, an LED or an OLED.

By using dual emitters as wavelength conversion materials, it is possible to achieve a reduction in the very pronounced reabsorption which otherwise occurs in such arrangements due to the long path of the radiation (as a result of repeated passage through the wavelength conversion region or the laser-active region). Using a dual emitter makes it possible to reduce reabsorption in the laser-active region (laser medium) and thus to obtain a higher efficiency laser.

The invention is not restricted by the description given with reference to the exemplary embodiments. Rather, the invention encompasses any novel feature and any combination of features, including, in particular, any combination of features in the claims, even if this feature or this combination is not itself explicitly indicated in the claims or exemplary embodiments.

The invention claimed is:

1. An optoelectronic apparatus comprising:
at least one wavelength conversion region which comprises at least one dual emitter as wavelength conversion material, wherein the wavelength conversion region converts primary radiation at least in part into secondary radiation,
wherein the dual emitter comprises a first electronic base state and a second electronic base state, together with a first electronically excited state and a second electronically excited state which is reachable from the first electronically excited state,
wherein the dual emitter further comprises an emission proceeding from the second electronically excited state into the second base state, and
wherein the dual emitter comprises molecules of the following general formulae:

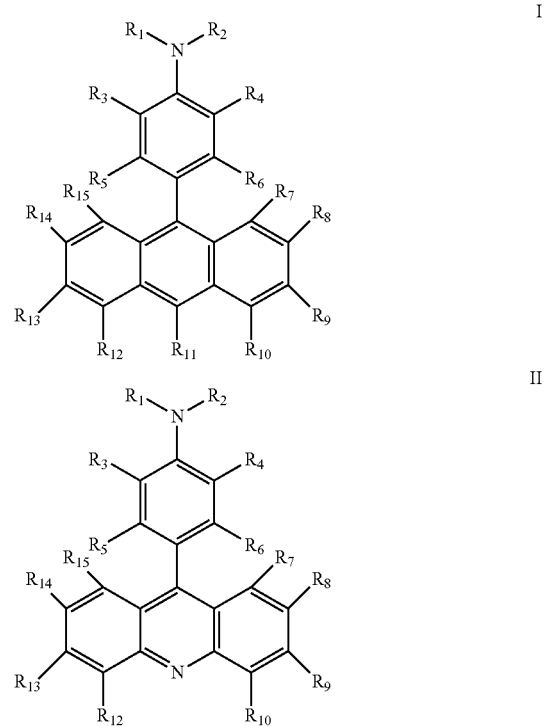

-continued

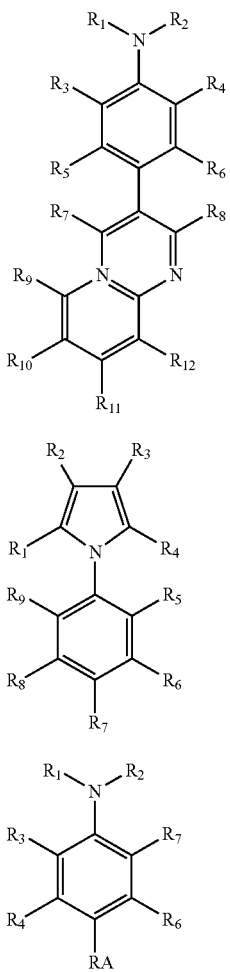

where RA and $R_1$ to $R_4$ are mutually independently selectable from hydrogen, alkyl or alkenyl groups, long-chain alkyl, alkoxy, long-chain alkoxy, cycloalkyl, haloalkyl, aryl, arylenes, haloaryl, heteroaryl, heteroarylenes, heterocycloalkylenes, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, ketoalkenyl, haloketoalkenyl, or part of a cyclic, aromatic or heteroaromatic system.

2. The optoelectronic apparatus according to claim 1, wherein a transition from the first electronically excited state into the second electronically excited state proceeds by intramolecular proton transfer (ESIPT) or intramolecular charge transfer (ICT).

3. The optoelectronic apparatus according to claim 1, wherein, in the dual emitter, a transition from the first electronically excited state into the second electronically excited state proceeds faster than a radiation-emitting decay proceeding from the first electronically excited state into the first electronic base state.

4. The optoelectronic apparatus according to claim 1, wherein a transition from the second electronic base state into the first electronic base state of the dual emitter proceeds faster than an excitation from the second base state into the second electronically excited state.

5. The optoelectronic apparatus according to claim 1, wherein the dual emitter exhibits keto-enol tautomerism inducible by intramolecular proton transfer.

6. The optoelectronic apparatus according to claim 5, wherein the dual emitter has the following general tautomeric limit formulae:

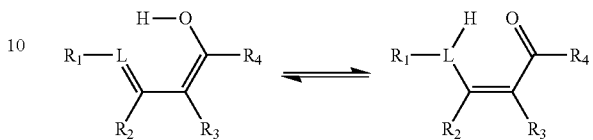

wherein L is either nitrogen, oxygen or sulfur, and $R_1$ to $R_4$ are mutually independently selectable from hydrogen, alkyl or alkenyl groups, long-chain alkyl, alkoxy, long-chain alkoxy, cycloalkyl, haloalkyl, aryl, arylenes, haloaryl, heteroaryl, heteroarylenes, heterocycloalkylenes, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, ketoalkenyl, haloketoalkenyl, or part of a cyclic, aromatic or heteroaromatic system, wherein the residues $R_1$ to $R_4$ have substituents, and wherein the substituents are mutually independently selectable from the same group as the residues $R_1$ to $R_4$.

7. The optoelectronic apparatus according to claim 1, wherein the dual emitter exhibits intramolecular charge transfer which is inducible between at least one electron acceptor group and an electron donor group.

8. The optoelectronic apparatus according to claim 1, wherein the dual emitter additionally emits radiation from the first excited electronic state.

9. The optoelectronic apparatus according to claim 1, wherein at least 75% of the primary radiation is converted into the secondary radiation.

10. The optoelectronic apparatus according to claim 1, wherein at least 98% of the primary radiation is converted into the secondary radiation.

11. The optoelectronic apparatus according to claim 1, wherein at least some of the primary and/or the secondary radiation passes repeatedly through the wavelength conversion region.

12. The optoelectronic apparatus according to claim 1, wherein the wavelength conversion region further comprises a matrix material.

13. The optoelectronic apparatus according to claim 1, wherein the optoelectronic apparatus comprises a primary radiation source selected from the group consisting of: organic light-emitting diodes (OLEDs), inorganic light-emitting diodes (LEDs), and surface emitters (VCSELs), and wherein the primary radiation source emits the primary radiation which is converted at least in part into the secondary radiation by the wavelength conversion region.

14. The optoelectronic apparatus according to claim 1, wherein the optoelectronic apparatus is an organic light-emitting diode (OLED), wherein the OLED further comprises a first electrode, a second electrode and a radiation-emitting region which differs from the wavelength conversion region, and wherein both the radiation-emitting region and the wavelength conversion region are arranged between the first and the second electrode.

15. The optoelectronic apparatus according to claim 1, wherein the optoelectronic apparatus is a laser, wherein the laser comprises a primary radiation source as pump radiation source, wherein the wavelength conversion region is arranged as a laser-active region between two at least partially reflective regions, and wherein the laser-active region is arranged in a beam path of the primary radiation source.

16. The optoelectronic apparatus according to claim 1, wherein the optoelectronic apparatus comprises a photoactive region on which the secondary radiation impinges.

* * * * *